(12) United States Patent
Goetz et al.

(10) Patent No.: US 6,499,658 B2
(45) Date of Patent: Dec. 31, 2002

(54) MULTIPLE-CASUALTY INCIDENT PATIENT TRACKING

(76) Inventors: John W. Goetz, 7602 Barringer Rd., Baton Rouge, LA (US) 70817; Chad J. Guillot, 12225 Wickwood Ave., Baton Rouge, LA (US) 70818

( * ) Notice: Subject to any disclaimer, the term of this patent is extended or adjusted under 35 U.S.C. 154(b) by 0 days.

This patent is subject to a terminal disclaimer.

(21) Appl. No.: 09/964,718

(22) Filed: Sep. 27, 2001

(65) Prior Publication Data

US 2002/0011518 A1 Jan. 31, 2002

Related U.S. Application Data

(63) Continuation of application No. 09/369,871, filed on Aug. 9, 1999, now Pat. No. 6,305,605.

(51) Int. Cl.$^7$ ............................................. G06F 17/60
(52) U.S. Cl. ............. 235/385; 235/462.01; 235/462.45; 705/5
(58) Field of Search ................. 235/385, 454, 235/462.01, 462.45, 462.46, 469, 472.01, 472.02, 462.13; 705/1, 2, 5, 22

(56) References Cited

U.S. PATENT DOCUMENTS

| | | | |
|---|---|---|---|
| 4,164,320 A | 8/1979 | Irazoqui et al. | 235/375 |
| 4,476,381 A | 10/1984 | Rubin | 235/375 |
| 4,857,713 A | 8/1989 | Brown | 235/375 |
| 4,857,716 A | 8/1989 | Gombrich et al. | 235/462 |
| 5,006,699 A | 4/1991 | Felkner et al. | 235/472 |
| 5,245,930 A | * 9/1993 | Williams | 104/120 |
| 5,291,399 A | 3/1994 | Chaco | 364/413 |
| 5,528,025 A | 6/1996 | Swintek | 235/472 |
| 5,596,652 A | 1/1997 | Piatck et al. | 382/115 |
| 5,760,704 A | 6/1998 | Barton et al. | 340/825 |
| 5,793,882 A | 8/1998 | Piatek et al. | 382/115 |
| 6,305,605 B1 | * 10/2001 | Goetz et al. | 235/385 |

* cited by examiner

*Primary Examiner*—Thien M. Le
*Assistant Examiner*—Daniel St. Cyr
(74) *Attorney, Agent, or Firm*—David L. Ray

(57) ABSTRACT

A method for tracking multiple injured victims at a multiple injury scene to provide information on their medical status and their location to emergency personnel and to treatment facilities, the method including examining the injured victims at the scene to determine the medical condition of the victims, attaching a tag to each of the victims to identify the victim and to indicate the medical condition of the victim, the tag having machine-readable information thereon indicating the identity and medical condition of the victim, and the tag having visually readable colors thereon indicating the urgency of treatment needed by the victim, scanning and transmitting the machine-readable information on each of the victims to victim transportation units and other emergency personnel at the scene to enable transport personnel to determine which victims are in most urgent need of transport to a medical treatment facility, and transmitting the machine-readable information on each of the victims to medical treatment facilities to which the victims may be transported.

20 Claims, 4 Drawing Sheets

MULTIPLE-CASUALTY INCIDENT PATIENT TRACKING

This application is a continuation of U.S. application Ser. No. 09/369,871, filed on Aug. 9, 1999, now U.S. Pat. No. 6,305,605.

BACKGROUND OF THE INVENTION

1. Field of the Invention

The present invention relates to a system and method for tracking injured people from the scene of the incident until their arrival at a hospital. In particular, the present invention relates to a system and method for accounting for and tracking injured people at a mass casualty incident such as an airplane crash scene or a chemical plant explosion from the scene of the incident to a hospital.

2. Description of the Related Art

An airplane crash, building bombing, chemical plant explosion, and other disasters resulting in large numbers of injured people at one location is referred to as a Multiple/Mass Casualty Incident (MCI). Such incidents greatly strain the resources of hospitals, emergency personnel, and other organizations such as local police responding to the needs of the victims of the disaster. Whether it's a fifty-unit rescue organization responding to a plane crash with over three hundred victims, or a two unit service responding to a wreck with fifteen victims, there is an urgent need to disseminate information concerning the medical status of the victims among the personnel treating the victims at the site or scene of the incident and to a hospital receiving the victims. Information about the total number of victims, the amount and type of available emergency equipment, and the amount and type of resources of local hospitals at the time of the incident is critical to prevent further loss of life, aggravation of injuries, and unnecessary pain and suffering.

Exemplary of the prior art are the following U.S. Pat. Nos.: 4,164,320; 4,476,381; 4,857,713; 4,857,716; 5,006,699; 5,291,399; 5,528,025; 5,596,652; 5,760,704 and 5,793,882.

SUMMARY OF THE INVENTION

In accordance with the present invention there is provided a system which enables emergency medical services, police departments, fire departments, hospitals, and government officials to electronically track a victim's medical status and location in a multiple injury incident in real-time to ensure that the victim receives the most appropriate and immediate medical treatment available. This system also allows for the immediate sharing of vital information with all responding agencies and members of the community who are affected by the incident. The system initiates data collection when the first emergency vehicle arrives at the scene of the incident and ends data collection when the last patient or victim has been delivered to the hospital. The term "patient" as used herein shall refer to victims of the multiple-casualty incident. All of such data is stored throughout the occurrence of the incident for review and analysis after all of the victims of the incident have been placed in hospitals or other treatment facilities. The system is based on a national standard of treatment incident which is classified as a Multiple/Mass Casualty Incident or a multiple injury incident.

The present invention has the following advantages:

a. Increases the accuracy of reporting the number of injured victims at a large accident and the severity of these victims in a real-time mode;

b. Accurately establishes and stores a timeline of patient care and removal from the scene of the incident that can be reviewed at a later date;

c. Reduces error and redundancy of resources at a multiple-casualty scene;

d. Provides accurate information to hospitals and other treatment facilities concerning the number, and medical status, of patients being sent to them and enables the facility, if necessary, to redirect the patient to a more appropriate facility;

e. Enables the agencies involved in providing help to the victims to have a real-time picture of the incident to provide the best response; and f. Provides a mechanism to collect and store data, on a national/international level, which can be used by others for statistical analysis or planning.

DESCRIPTION OF THE PREFERRED EMBODIMENTS

Figure 1:
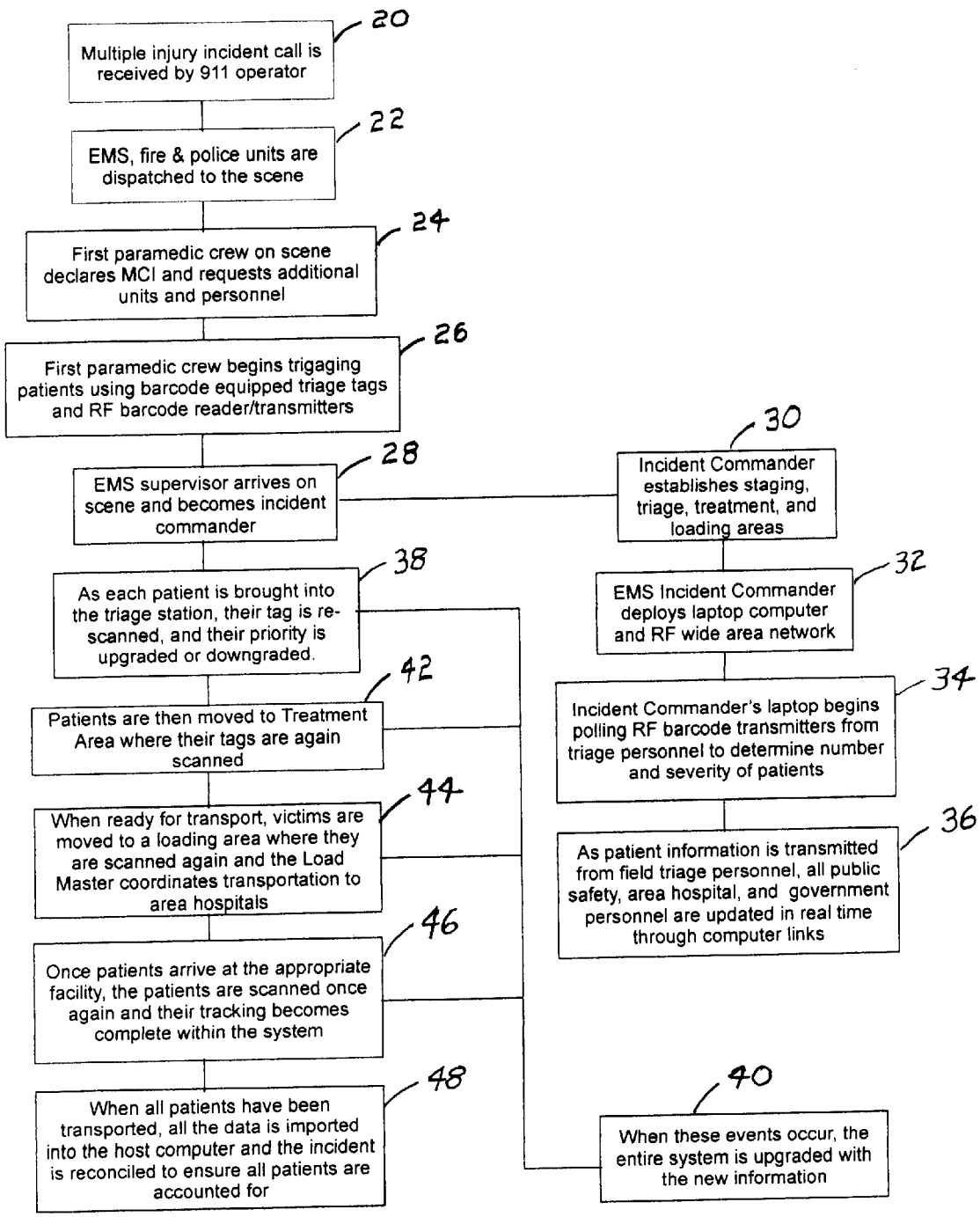
FIG. 1 is a flow diagram showing the overall flow of events that would occur at the scene of a multiple-casualty incident as a result of implementing the present invention.

Referring now to FIG. 1, there is shown the overall flow of events that would occur at the scene of a multiple-casualty incident as a result of implementing the present invention. Normally, as indicated in block 20 of FIG. 1, a 911 telephone call would be received by a 911 operator indicating a multiple injury incident.

As indicated in block 22, EMS (emergency medical service), fire, and police units are dispatched to the scene of the incident. EMS units have Emergency Medical Technicians or paramedic crews in each unit to assess the medical condition of the victims of the MCI and to render emergency medical treatment in the field. EMS units and personnel are sometimes referred to herein as paramedic crews.

As indicated in block 24, the first EMS or paramedic crew unit arrives at the scene and immediately declares an MCI. Additional EMS units, an EMS supervisor and personnel, and fire control and police units are requested by the EMS personnel in the first unit by radio as needed.

As indicated in block 26, the paramedics in the first unit, and additional EMS units summoned by the first EMS unit paramedics, begin the task of finding and assessing the condition of the victims and triaging the victims. By triaging is meant that victims are placed in categories based on the urgency of treatment needed. The medical condition of a victim is assessed at the scene of the incident by the emergency personnel, preferably the EMS paramedics, and the emergency personnel record the victim's condition on the front side a card or tag generally indicated by the numeral 27 shown in FIG. 2. Treatment of victims is minimal at this stage and only an assessment of the condition of the victims at the scene of the incident is made and indicated on the front side of tag 27.

Figure 2:
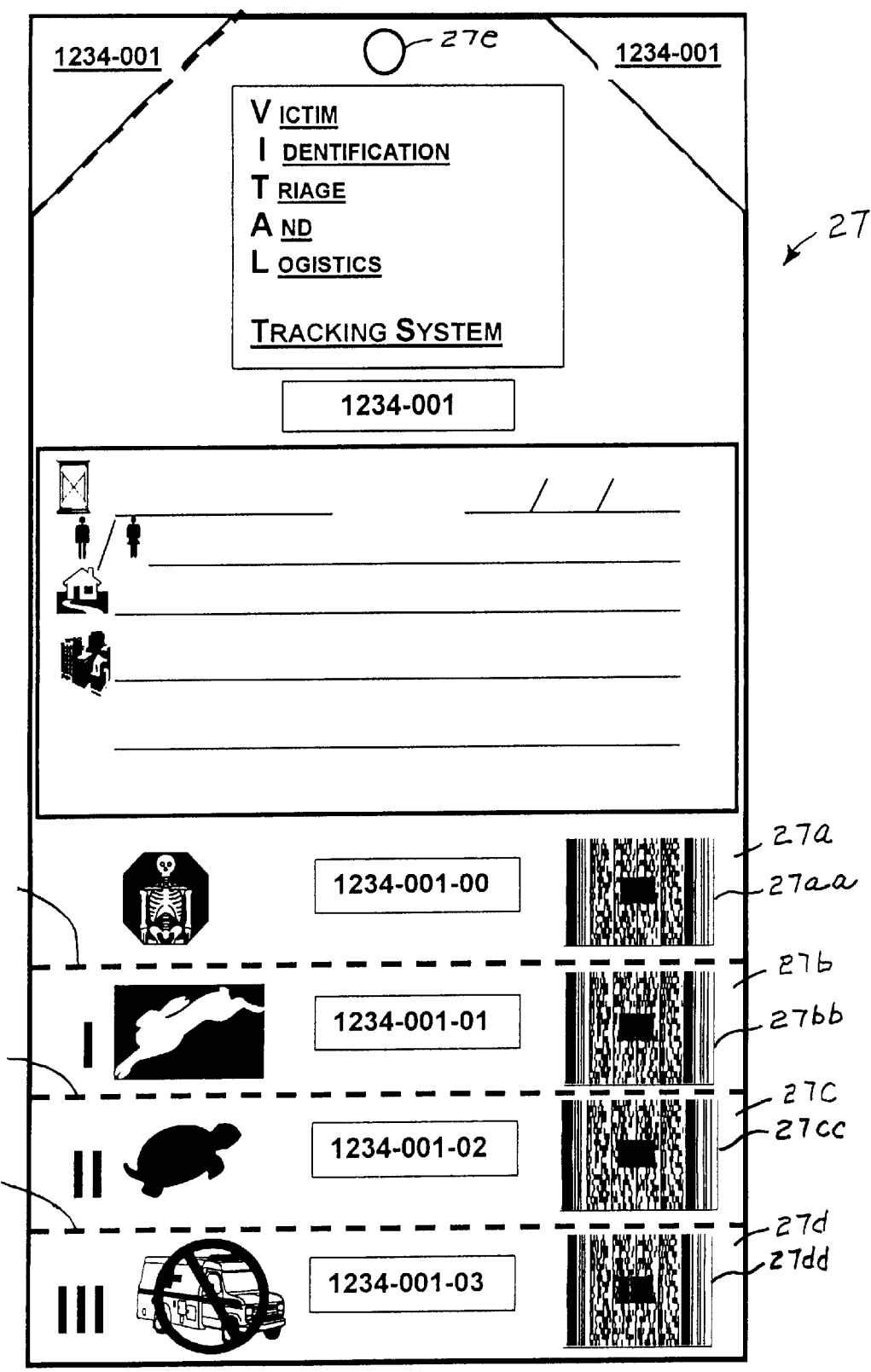
FIG. 2 is a plan view of the front side of a tag that may be attached to a victim.

The front side of tag 27 shown in FIG. 2 has four labels 27a, 27b, 27c and 27d which are connected to tag 27 at perforated lines 25a, 25b, and 25c. Perforated lines 25a, 25b, and 25c enable labels 27b, 27c, and 27d to be manually torn off and removed from tag 27 by emergency personnel.

The four labels 27a, 27b, 27c and 27d contain information corresponding to the urgency of treatment needed by a victim to which tag 27 is connected. To indicate the urgency of treatment needed by a victim, labels 27d, 27c, and/or 27b are torn off of tag 27 along perforated lines 25c, 25b, or 25a by emergency personnel and removed from tag 27, leaving one or more labels 27d, 27c, 27b, and/or 27a. The bottom or lowest remaining label 27a, 27b, 27c or 27d on tag 27 corresponds to the urgency of treatment of the victim to which the tag 27 is connected.

Each of the labels 27a, 27b, 27c, and 27d is preferably color coded for quick visual identification of the medical condition of the victim. Color coding of labels attached to victims such as labels 27a, 27b, 27c, and 27d is known in the art. Commonly, the color red is used to indicate that the victim is in critical condition and in the most urgent need of treatment, yellow is used to indicate the victim is in urgent need of treatment, green is used to indicate that treatment may be delayed, and black or gray is used to indicate the victim is dead or dying. Therefore, label 27a is preferably black, label 27b is preferably red, label 27c is preferably yellow, and label 27d is preferably green.

A symbol may also be used on each of the labels 27a, 27b, 27c, and 27d in addition to color for quick and easy visual identification of the urgency of treatment needed by the victim to whom the tag 27 is attached. Symbols such as a skeleton shown on label 27a, a rabbit shown on label 27b, a turtle shown on 27c, and a crossed-out EMS vehicle shown on label 27d may also be used to quickly visually indicate to other emergency personnel transporting the victim of the urgency or priority of transporting the victim to a hospital or other treatment facility.

For example, the skeleton and black color on label 27a would indicate that the victim to which the label is attached is deceased, transport is not urgent, and transport to a morgue or other temporary deceased victim storage or holding facility is appropriate. The rabbit symbol and red color on label 27b would indicate, for the victim to which the label is attached, that transport to a treatment facility is extremely urgent and is of top or first priority. The turtle symbol and yellow color on label 27c would indicate, for the victim to which the label is attached, that transport to a treatment facility is urgent but is of secondary priority to victims having a red label 27b with a rabbit symbol there. The crossed-out EMS vehicle symbol and green color on label 27d would indicate that the victim is in good medical condition and is not in need of transport by EMS personnel to a treatment facility.

In accordance with the present invention, each label 27a, 27b, 27c, and 27d also has a conventional individual bar code 27aa, 27bb, 27cc, and 27dd placed thereon. The individual bar codes 27aa, 27bb, 27cc, and 27dd include a victim identification number and indicia indicating the urgency of treatment needed by the victim. The victim identification number is also printed on the individual labels 27a, 27b, 27c, and 27d along with a number corresponding to the medical condition of the victim. As shown in FIG. 2, the victim identification number is printed on labels 27a, 27b, 27c, and 27d of tag 27 adjacent to the left side of the bar codes 27aa, 27bb, 27cc, and 27dd as the series of numbers "1234-001" with the medical condition of the victim being indicated by the last two numerals following the series of numerals "1234-001". Thus, on label 27a, the printed number "1234-001-00" visually indicates that the victim having label 27a has the identification number "1234-001" and has medical condition indicated by the numbers "-00" following the identification number "1234-001", which is the medical condition associated with label 27a. Likewise, on label 27b, the printed number "1234-001-01" visually indicates that the victim having label 27b connected its body has the identification number "1234-001" and has medical condition indicated by the numbers "-01" following the identification number "1234-001", which is the medical condition associated with label 27b; on label 27c, the printed number "1234-001-02" visually indicates that the victim having this label has the identification number "1234-001" and has medical condition indicated by the numbers "-02" following the identification number "1234-001", which is the medical condition associated with label 27c; and on label 27d, the printed number "1234-001-03" visually indicates that the victim having this label has the identification number "1234-001" and has medical condition indicated by the numbers "-03" following the identification number "1234-001", which is the medical condition associated with label 27d.

Figure 4:
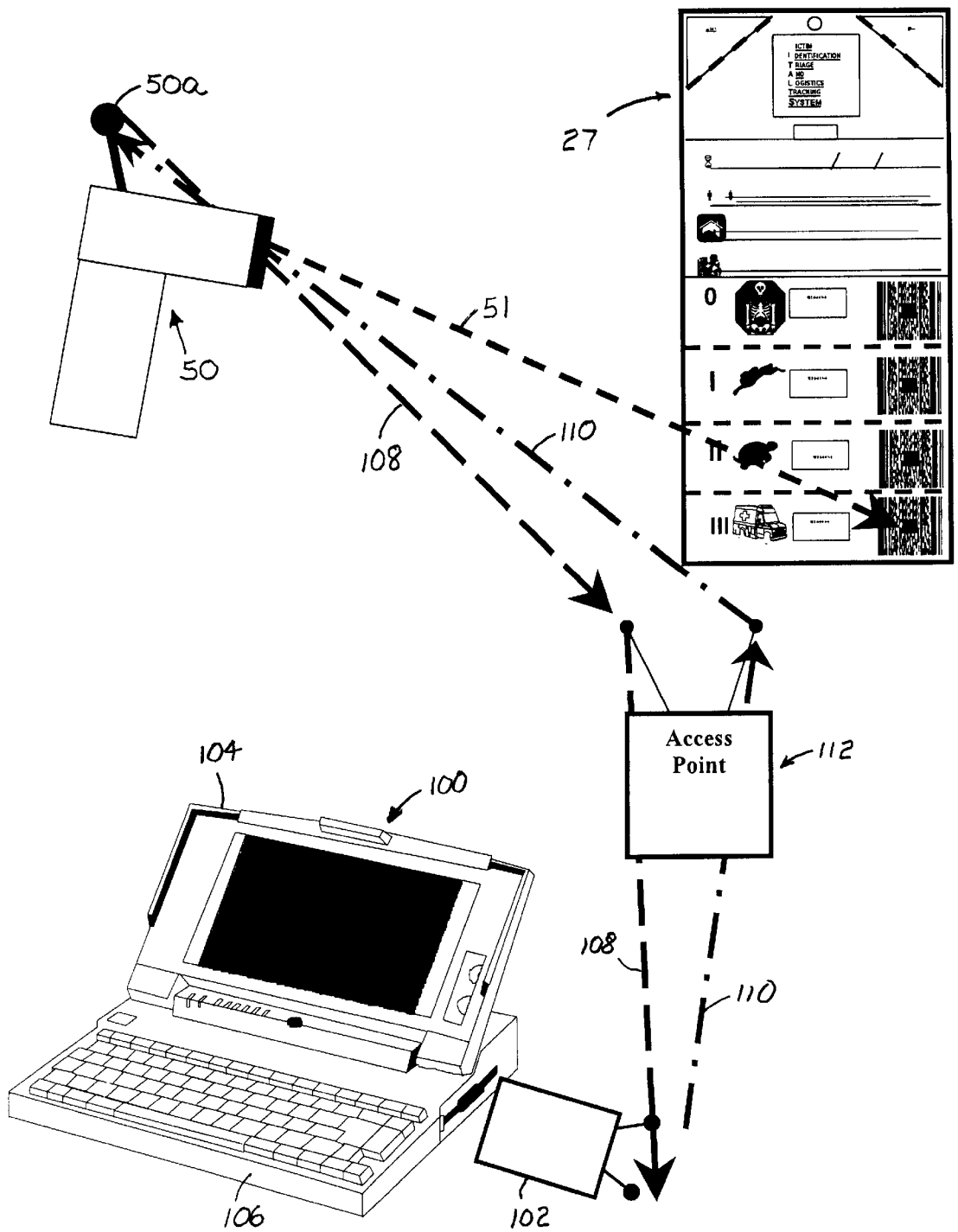
FIG. 4 is a schematic view of the wireless communication network of the invention.

Bar codes 27aa, 27bb, 27cc, and 27dd are well known in the art and can be scanned or read by a conventional hand-held portable bar code electronic scanner generally indicated by the numeral 50 in FIG. 4 by light beams 51 which is also well known in the art. Scanner 50 has a conventional date and time indicator incorporated therein which indicates the date and time that an individual bar code 27aa, 27bb, 27cc or 27dd is scanned by scanner 50, and a conventional data storage device or memory for storing the date and time and information on the bar code being scanned. Each scanner 50 also has a conventional identification number to identify the particular scanner being used to scan a bar code. U.S. Pat. No. 5,596,652 discloses such bar codes and scanners in detail and is hereby incorporated by reference.

After the emergency personnel have assessed the medical condition of a victim of the MCI at the scene of the MCI and indicated the condition of the victim by removing the appropriate labels 27b, 27c or 27d from tag 27 and scanning the bottom or lowest remaining label 27a, 27b, 27c or 27d on tag 27, tag 27 is attached by string or wire to the ankle or wrist of the assessed victim by extending the string or wire through the hole 27e at the top of tag 27 and securing tag 27 to the victim's arm or leg. Therefore, the urgency of treatment needed by the victim can be determined visually by looking at the bottom or lowest remaining label 27a, 27b, 27c or 27d on tag 27. Such a procedure allows for an appropriately rapid emergency response for treatment of each victim and works for the good of the many victims.

The front side of tag 27 may contain a plurality of horizontal lines shown in the approximate middle thereof for entering any notes desired by emergency personnel attending the victim of the MCI.

The bar code on the bottom or lowest remaining label 27a, 27b, 27c or 27d is then scanned by the portable hand-held, battery powered scanner 50 to record the patient number and condition indicated on the bottom or lowest remaining label 27a, 27b, 27c or 27d. This scan is the initial or first scan of the victim and will indicate that the victim has not been brought to the Triage Area since it is the first scan of the victim recorded in computer 100 as indicated by the time recorded with the scan. The data scanned by scanner 50 from the appropriate individual bar code 27aa, 27bb, 27cc, or 27dd scanned on tag 27, which includes a patient ID number, the patient's condition, and the identification number of the particular scanner 50 that was used to scan the bar code, and the time and date of the scan, is recorded in the memory of each scanner 50 used at the MCI scene for transmission to a computer generally indicated by the numeral 100 in FIG. 4.

As indicated in block 28 of FIG. 1, an EMS supervisor arrives at the MCI scene with a conventional RF equipped mobile or lap-top computer 100 shown in FIG. 4 and becomes the Incident Commander. The Incident Commander is responsible for supervising all emergency personnel at the scene of the incident and is appointed the commanding officer on the scene.

As indicated in block 30 of FIG. 1, the Incident Commander establishes staging, triage, treatment, and victim loading areas at the scene of the incident. In the triage area, victims are re-evaluated and can be separated into different treatment areas, which are utilized to treat and stabilize victims at the scene of the incident. There may be several different treatment areas established to treat different types of victim injuries and degrees of severity of injuries. The loading area is a holding area where victims are assigned to ambulances to be transported to receiving facilities. Each of the triage, treatment, and loading areas will have a lightweight, lap-top computer similar or identical to computer 100, and will constantly provide updates of victim information to the Incident Commander.

As indicated in block 32 of FIG. 1, the EMS Incident Commander deploys the mobile computer equipment generally indicated by the numeral 100 in FIG. 4. As shown in FIG. 4, computer 100 includes a transceiver or RF sending and receiving unit or wireless radio modem 102 well known in the art. As is known in the art, wireless radio modem 102 is a device used in computers including laptop, notebook, and hand-held computers to access wireless local and wide area networks. Wireless radio modems such as modem 102 generally fit in a card slot in the computer 100 and have a small antenna through which the modem 102 transmits and receives RF data. External antennas can be added to modem 102 to increase the transmission and receiving range. Modem 102 typically transmits and receives data in one of the following bandwidths:

902–928 MHz
2.4–2.483 MHz
5.15–5.35 MHz
5.725–5.875 MHz

Computer 100 makes RF contact with the transceiver 50a of individual scanners 50 through modem 102 to query or read data that is scanned and stored in each individual scanner as indicated by the dotted lines 108 and 110. Computer 100 includes a video display 104 and a keyboard or manual input device 106.

A conventional access point well known in the art is generally indicated by the numeral 112. Access point 112 is a schematic representation of the point where nodes (computers such as computer 100) in a wireless local or wide area network gain access to the scanners 50 or other computers at the scene of the incident. Access point 112 may also be used to extend the range at which RF transmissions may be sent and retrieved.

As indicated in block 34 of FIG. 1, the Incident Commander begins polling RF bar code transmitters on scanners 50 from triage personnel, retrieving data from all of the scanners 50 in the incident field by contacting or querying each scanner 50 utilized through RF signals 108 and 110, to determine the number and severity or urgency of treatment of victims or patients. Once the query is complete and the RF connections 108 and 110 are established with each scanner 50 as shown schematically in FIG. 4, the information stored on each individual scanner 50 can be transmitted by RF signals back to computer 100 in real time.

The mobile computer 100 that is used by the EMS Incident Commander displays a complete picture of how many victims are involved in the incident along with their medical status with a break down of the different severity of injuries that the agency is dealing with. This information-is a real-time view of the scene and aids the EMS Incident Commander in initiating an appropriate response.

As indicated in block 36 of FIG. 1, the data from the scanners 50 received by mobile computer 100 is transmitted and shared with emergency units in the immediate incident area dealing with the incident to inform them of the status of the victims on the MCI scene. Information can be relayed to area hospitals, disaster centers, or anywhere a receiver can be set up. As the command post is established, all public safety agencies are linked via a wireless network, so that each agency can observe the status of the incident in real time. Government and hospitals equipped with this system will also be able to see the progression of the incident, allowing hospital personnel significantly greater time to prepare for the arrival of patients. Moreover, because this system shares its information, no one hospital will be unnecessarily burdened with excessive or severe injuries.

As indicated in block 38, as victims having tags 27 connected thereto are moved from the incident location to the triage area, the bar code on the bottom or lowest remaining label 27a, 27b, 27c or 27d of the tag 27 on the victim will be re-scanned by scanners 50 to acknowledge their progression, and the entire system is upgraded with the new information as indicated in block 40 by transmitting scanned data to computer 100. This scan is the second scan of the victim and will indicate that the victim is in the Triage Area since it is the second scan of the victim recorded in computer 100 as indicated by the time recorded with the scan.

Triage personnel will then re-assess the victims's injuries, and if indicated, raise or lower their treatment priority. To raise or lower the treatment priority, tag 27 has a back side shown in FIG. 3. The back side of tag 27 has printed thereon information indicating to emergency personnel that the back side of tag 27 that emergency personnel should "Upgrade/Downgrade Patients on This Side" printed thereon.

The back side of tag 27 contains another set of the four labels 27h, 27i, 27j and 27k having the same bar codes 27aa, 27bb, 27cc or 27dd, color, and symbols as labels 27a, 27b, 27c, and 27d as the front side of tag 27 shown in FIG. 2. The four labels 27h, 27i, 27j and 27k are printed on the back side of tag 27 and are separated by printed lines 25d, 25e, and 25f. To indicate an upgrade or downgrade in the urgency of treatment needed by a victim, the labels 27k, 27j, 27i, or 27h is scanned by by emergency personnel with scanner 50, the tag 27 which is connected to the victim is removed, and a new tag 27 with a new patient identification number is attached to the victim as described above in connecting the first tag 27 to a victim. The person attaching the new tag 27 removes the appropriate labels as explained above from the front side of new tag 27 shown in FIG. 2, and then scans the bottom or lowest remaining label 27a, 27b, 27c or 27d on tag 27 corresponding to the upgraded or downgraded urgency of treatment of the victim to which the new tag 27 is connected. The upgraded or downgraded victim has a new identification number since a new tag 27 has been attached to the victim and scanned with scanner 50.

Figure 3:
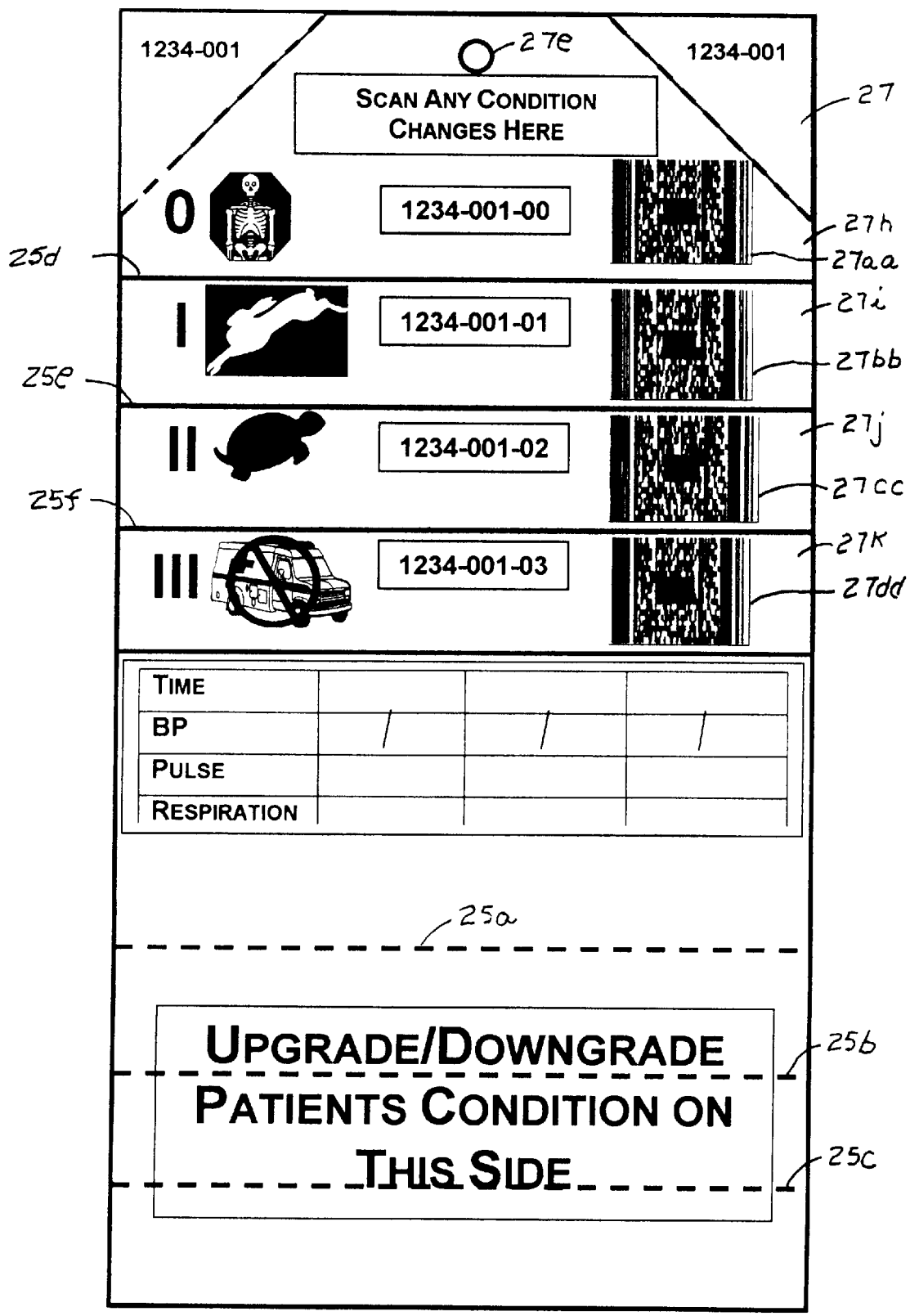
FIG. 3 is a plan view of the back side of the tag shown in FIG. 2.

The back side of tag 27 shown in FIG. 3 may contain a plurality of rectangular boxes or blocks lines shown in the approximate middle thereof for entering any notes desired by emergency personnel attending the victim of the MCI.

As indicated in block 40 of FIG. 1, the bar code 27*aa,* 27*bb,* 27*cc* or 27*dd* on the bottom or lowest remaining label on the back side of tag 27 then scanned by hand-held scanner 50 to record the patient number and urgency of treatment indicated on the lowest remaining label, ensuring that no patient can be lost or unaccounted for. As explained previously in the explanation of the front side of tag 27 shown in FIG. 2, the urgency of treatment of the victim can be quickly determined visually by looking at the color or symbol of the bottom or lowest remaining label 27*h,* 27*i,* 27*j* or 27*k* on the back side of tag 27 shown in FIG. 3.

As indicated in block 42 of FIG. 1, patients are then moved to the Treatment Area and their tags are again scanned, and the entire system is upgraded with the new information as indicated in block 40 by transmitting the latest scanned data to computer 100. This scan is the third scan of the victim and will indicate that the victim is in the Treatment Area since it is the third scan of the victim recorded in computer 100 as indicated by the time recorded with the scan, and the entire system is upgraded with the new information as indicated in block 40 by transmitting scanned data to computer 100.

As indicated in block 44, the next step would be to transport the victims to the Loading Area where a Load Master is appointed to supervise the operation of the Loading Area. In the Loading Area, victims are loaded into a waiting ambulance that will transport them to an area hospital, and their tags are again scanned, and the entire system is upgraded with the new information as indicated in block 40 by transmitting the latest scanned data to computer 100. This scan is the fourth scan of the victim and will indicate that the victim is in the Loading Area since it is the fourth scan of the victim recorded in computer 100 as indicated by the time recorded with the scan. The Loading Area is a very important stage for the smooth operation of the MCI in that patients must be transported to an appropriate facility and it must be determined by the Load Master that the facility receiving the patient has the spaces for the patient. The Load Master is responsible for assigning victims to ambulances for transport. The Load Master must frequently check the capacity of local hospitals to receive more victims. The Load Master is equipped with a notebook laptop computer equipped similar or identical to computer 100 which displays information from the hospitals regarding the number of patients they can receive and how many patients they are currently treating.

As indicated in block 46, once the patient arrives at the hospital, the patient's tag is scanned by scanner 50, and the entire system is upgraded with the new information as indicated in block 40 by transmitting scanned data to computer 100. Arrival of the victim at the hospital marks the final step in the tracking process. This scan is the fifth and final scan of the victim or patient and will indicate that the victim is in the hospital since it is the fifth scan of the victim recorded in computer 100 as indicated by the time recorded with the scan.

The MCI incident is continuously reconciled to track all victims at the scene of the incident. As indicated in block 48 of FIG. 1, when all victims of the MCI have been transported to a hospital, and all data has been transmitted and stored into computer 100, the MCI incident is reconciled to ensure that all patients are accounted for.

Although the preferred embodiments of the invention have been described in detail above, it should be understood that the invention is in no sense limited thereby, and its scope is to be determined by that of the following claims:

What is claimed is:

1. A method for tracking multiple injured victims at a multiple injury scene to provide information on their medical status and their location to emergency personnel and to treatment facilities, the method comprising sequentially the steps of:
   a. examining the injured victims at said scene to determine the medical condition of said victims;
   b. attaching a tag to each of said victims to identify said victim and to indicate said medical condition of said victim, said tag having visual and machine-readable information thereon indicating the identity and medical condition of said victim;
   c. providing victim transportation units at said scene for transporting said victims to medical treatment facilities; and
   d. electronically scanning and transmitting said machine-readable information on each of said victims to emergency personnel at said victim transportation units at said scene to enable emergency personnel at said victim transportation units to determine which victims and the number of victims that are in most urgent need of transport to a medical treatment facility.

2. The method of claim 1 wherein said machine-readable information on each of said victims is transmitted to medical treatment facilities to which the victims may be transported.

3. The method of claim 1 wherein said tag has visually readable colors thereon indicating the urgency of treatment needed by the victim.

4. The method of claim 1 wherein said tag has symbols thereon indicating the urgency of treatment needed by the victim.

5. The method of claim 1 wherein said machine-readable information on each of said victims is transmitted to emergency personnel at said scene.

6. The method of claim 1 wherein said tag has numbers thereon to identify the victim to which the tag is connected.

7. The method of claim 1 wherein said machine-readable information is a bar code.

8. A method for determining urgency of treatment needed by victims at a multiple injury scene comprising sequentially the steps of:
   a. examining the injured victims at said scene to determine a medical condition of said victims;
   b. attaching a tag to each of said victims to identify said victim and to indicate urgency of treatment needed by said victim, said tag having visual and machine-readable information thereon indicating the identity and urgency of medical treatment needed by said victim;
   c. electronically scanning and transmitting said machine-readable information on to a computer at said scene to track the location of said victims at said scene; and
   d. transporting said victims to medical treatment facilities based on the urgency of treatment indicated on said tags.

9. The method of claim 8 wherein said machine-readable information on each of said victims is transmitted to medical treatment facilities to which the victims may be transported.

10. The method of claim 8 wherein said tag has visually readable colors thereon indicating the urgency of treatment needed by the victim.

11. The method of claim 8 wherein said tag has symbols thereon indicating the urgency of treatment needed by the victim.

12. The method of claim 8 wherein said machine-readable information on each of said victims is transmitted to emergency personnel at said scene.

13. The method of claim 8 wherein said tag has numbers thereon to identify the victim to which the tag is connected.

14. The method of claim 8 wherein said machine-readable information is a bar code.

15. A method for determining urgency of treatment needed by victims at a multiple injury scene comprising the steps of:
   a. examining the injured victims at said scene to determine a medical condition of said victims;
   b. attaching a tag to each of said victims to identify said victim and to indicate urgency of treatment needed by said victim, said tag having visual and machine-readable information thereon indicating the identity and urgency of medical treatment needed by said victim;
   c. electronically scanning and transmitting said machine-readable information on to a computer at said scene to track the location of said victims at said scene; and
   d. transporting said victims to a triage area at said scene;
   e. examining said victims at said triage area to determine the medical condition of said victims;
   f. updating said machine-readable information on said tag to indicate any change in urgency of treatment needed by said victim;
   g. electronically scanning and transmitting said machine-readable information on to said computer at said scene to track the location of said victims at said scene; and
   h. transporting said victims to medical treatment facilities based on urgency of treatment indicated on said tags.

16. The method of claim 15 wherein said tags have removable labels containing said machine-readable information thereon.

17. The method of claim 16 wherein said victims are moved to a treatment area at said scene prior to transporting said victims to medical treatment facilities, and said machine-readable information on said tags is electronically scanned and transmitted to said computer.

18. The method of claim 17 wherein said victims are moved from said treatment area to a loading area prior to transporting said victims to medical treatment facilities, and said machine-readable information on said tags is electronically scanned and transmitted to said computer.

19. The method of claim 18 wherein said machine-readable information on each of said victims is transmitted to medical treatment facilities to which the victims may be transported.

20. The method of claim 19 wherein said machine-readable information is a bar code.

* * * * *